(12) United States Patent
Gilliam et al.

(10) Patent No.: US 9,375,654 B1
(45) Date of Patent: Jun. 28, 2016

(54) ALGAE GROWTH

(76) Inventors: Charles David Gilliam, Baton Rouge, LA (US); Stefanie Renee Gilliam, Baton Rouge, LA (US)

( * ) Notice: Subject to any disclaimer, the term of this patent is extended or adjusted under 35 U.S.C. 154(b) by 745 days.

(21) Appl. No.: 13/326,549

(22) Filed: Dec. 15, 2011

(51) Int. Cl.
*C12N 1/12* (2006.01)
*B01D 1/22* (2006.01)

(52) U.S. Cl.
CPC ... *B01D 1/22* (2013.01); *C12N 1/12* (2013.01)

(58) Field of Classification Search
USPC ............. 435/41; 159/13, 27, 44, 49; 165/115, 165/914; 202/236; 203/10, 72, 89, 100; 137/561
See application file for complete search history.

(56) References Cited

U.S. PATENT DOCUMENTS

| 6,579,714 B1 * | 6/2003 | Hirabayashi ........... C12M 21/02 435/101 |
| 2007/0048848 A1 * | 3/2007 | Sears ............................ 435/134 |

OTHER PUBLICATIONS

Karube (Biotechnological Reduction of CO2 Emissions, 1992.*
Schenk, Peer M., et al; "Second Generation Biofuels: High-Efficiency Microalgae for Biodiesel Production"; Bioenerg. Res. (2008) 1:20-43.
Melis, Anastasios, et al; "Hydrogen Production. Green Algae as a Source of Energy"; Plant Physiology, Nov. 2001, vol. 127, pp. 740-748.
Brennan, Liam, et al; "Biofuels from microalgae—A review of technologies for production, processing, and extractions of biofuels and co-products"; (2009), doi: 10.1016/j.rser.2009.10.009.
Benemann, John R.; "Biofixation of CO2 and Greenhouse Gas Abatement with Microalgae-Technology Roadmap"; Final Report Submitted to the U.S. Department of Energy National Energy Technology Laboratory and Steering Committee of the International Network n Biofixation of CO2 and Greenhouse Gas Abatement with Microalgae; Jan. 14, 2003; pp. 1-29.
Kratz, William A., et al; "Photosynthesis and Respiration of Three Blue-Green Algae"; Department of Zoology, University of Texas, Austin 12, Texas, pp. 275-280; Jan. 19, 1955.

* cited by examiner

*Primary Examiner* — Kagnew H Gebreyesus
*Assistant Examiner* — Nghi Nguyen
(74) *Attorney, Agent, or Firm* — Roy Kiesel Ford Doody & Thurmon

(57) ABSTRACT

An apparatus and method are disclosed for controlling the thickness of a flowing algae film. The algae film flow may be gravity-induced or the result of an alternative force. The algae is deposited on an upper end of a flow surface where a relatively thick layer of the film forms. The algae film flows over a fluid dispersal region where the surface area is expanding, which results in thinning of the film thickness. The fluid then flows over an active region where the surface area is designed to control the fluid film thickness. While in the active region, the algae film may absorb carbon dioxide, while releasing water vapor. Hydrogen gas may be captured from the process, as well.

17 Claims, 7 Drawing Sheets

Algae Growing Device

Hydrogen Production by Algae

Solar Distillation

ALGAE GROWTH

FIELD OF THE INVENTION

Figure 1:
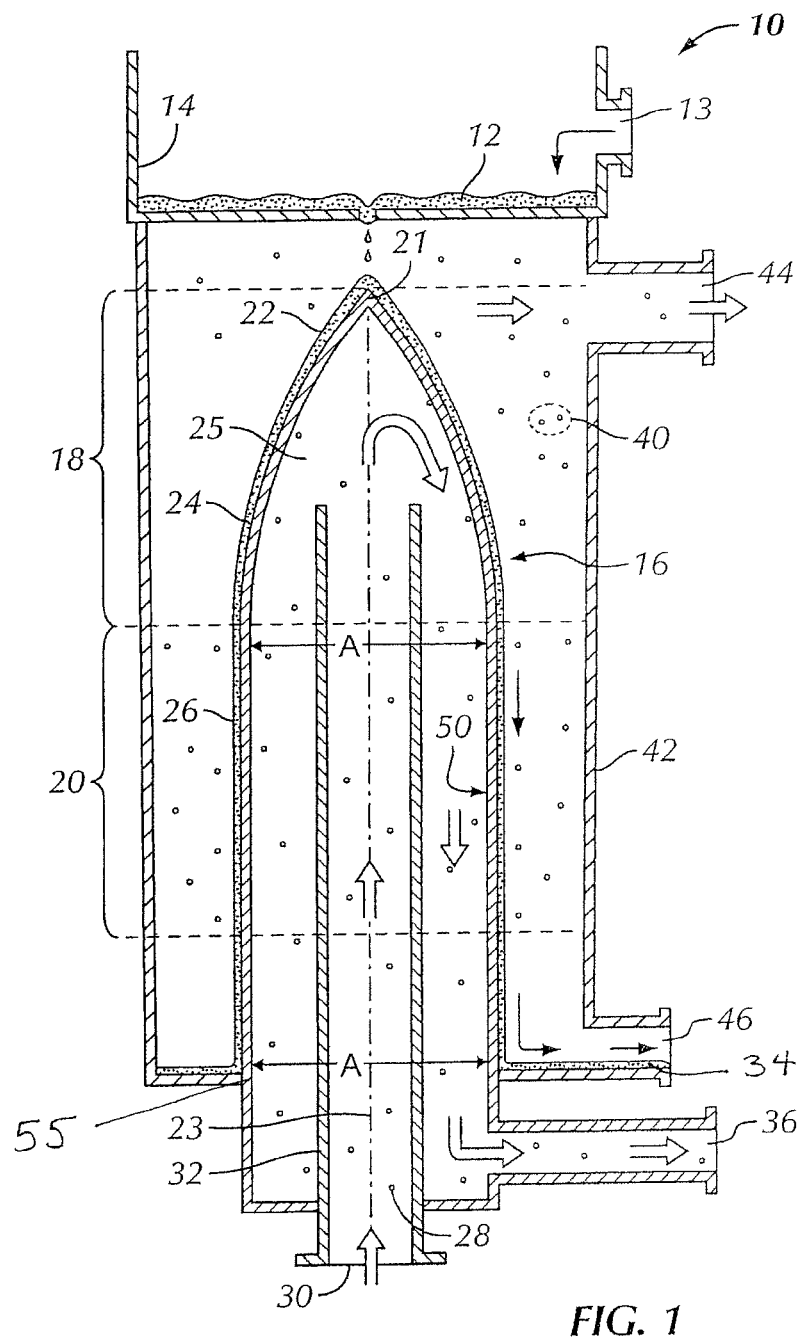

The present invention relates to a falling film evaporation, and more generally to a solid, flowing fluid film surface configured to manipulate and control the thickness of the fluid film flowing over the surface. The invention further relates to a method of controlling the thickness of a fluid film flowing over a solid surface. In particular, the present invention relates to an algae growth device that may be used for carbon capture, hydrogen production, or both. The invention also particularly relates to a solar distillation device.

PRIORITY CLAIM

This application is a continuation-in-part of U.S. application Ser. No. 12/953,058 filed on Nov. 23, 2010.

BACKGROUND OF THE INVENTION

A variety of devices has been constructed to create a thin flowing laminar fluid film. Falling film evaporators are a common example. An evaporator is a device designed to convert a liquid into a gas. Evaporation may be desired for various reasons, including for the distillation or purification of a liquid such as water. Seawater may be converted into potable water using evaporative technology, and this application is particularly important given the growing demand for potable water.

In a falling film evaporator, contaminated liquid is supplied to generally vertical heat exchange tubes. For example, in a seawater purification evaporator of this type, the seawater is the input. Seawater flows down vertical tubes while heat— typically in the form of steam—is supplied to the area outside the tubes. By allowing only a thin film of seawater to flow down the tubes, the heat transferred to the water is sufficient to evaporate some of the water. This water vapor, which is now pure water, rises up the center part of the tube. The vapor is then collected in some fashion and condensed to produce pure water.

Falling film evaporators work best when the flowing film thickness is maintained at a desired thickness. Returning to the seawater evaporator example, a relatively thin film is desired so that maximum evaporation will occur. If the film is too thick, evaporation will be inhibited. If the film is too thin, all the water will evaporate, leaving the tube surface dry. The latter situation can be damaging because of the combination of the high temperature tube surface with the various salts and other contaminants left behind by the evaporation. Hard scale deposits can result, and such scale can be effectively baked onto the tubes. This scale can be hard to remove, can reduce the heat transfer capability of the tubes, and can cause localized tube corrosion, particularly where the deposited materials are corrosive. For this reason, it is important to prevent drying of the tube surfaces in a falling film seawater evaporator.

One means used to avoid drying of the tube surface is to increase the flow rate of the fluid. By flowing more seawater down the tubes, there is less risk of the tubes drying. However, this also means the film layer will be thicker, which tends to reduce the evaporation rate. To offset this reduced thermal efficiency, a seawater falling film evaporator may employ a higher temperature. That is, rather than heating the tubes to 140° F., which is considered an optimal temperature for evaporation without significant scale adhesion to the heat transfer surface, an evaporator using higher seawater flow rates may need to raise the temperature substantially above this point. That increased heating will produce more evaporation, but it also will result in more baked on scale on the tubes. These trade offs render the falling film evaporator much less desirable as a means for purifying seawater.

In some applications, it may be desirable to evaporate the flowing fluid quickly within a particular region of the apparatus. For example, some liquids may contain certain entrained or dissolved gasses with relatively low flash points. It may be desired to selectively evaporate off these materials so that each can be separately handled. This operation is difficult to achieve in a conventional falling film evaporator. To achieve this result, long tubes may be needed and separate heating regions used along the tubes.

A somewhat new use of flowing film technology involves use of thin films of algae to capture carbon dioxide from the atmosphere. Algae use light and carbon dioxide to create energy, oxygen, and other products. Algae have been identified as a potentially important means of capturing carbon, that is, by removing carbon dioxide from the air.

In a falling film algae carbon capture apparatus, a thin film of algae may flow through an area exposed to light. Carbon dioxide rich air may be fed into the apparatus in the lighted region. The carbon dioxide is consumed by the algae which then flows past the lighted region and is further processed to remove any desired by products of the operation. For this process to work well, it is important to have the algae at a warm temperature, and that means some evaporation will occur. It is also desirable to maintain the algae at a constant film thickness to better facilitate the carbon capture.

These potential uses of falling film technology and the inherent trade offs presented by the use of a falling film evaporator to purify seawater or other contaminated liquids identify an important need. There is a need for an improved falling film apparatus and method that will obtain the potential benefits without the undesirable consequences. The present invention provides just such an apparatus and method.

SUMMARY OF THE INVENTION

The present invention provides a geometric solution to the problems noted above. A member is disclosed the serves the function of the falling film evaporator tube briefly described above. This member, however, is not an open-ended tube. It is closed on one end, that is, on the upper end in a vertical application. The liquid is deposited on the closed end and then flows down the outside surface of the member. The second end of this member, which is the lower end in a vertical application, may be open or closed. If open, the second end may allow the injection of a heated fluid into an inner chamber, thus heating the surface of the member. This operation is different from the typical falling film evaporator, which supplies heat to the area outside the tubes. In the present invention, if heat is supplied, it is supplied to the inside of the fluid flow member. The fluid to be processed flows down the outside of the member, not down the inside of a tube.

The present invention employs at least two distinct fluid flow regions: a fluid dispersal region and an active region. The fluid dispersal region has a rapidly expanding surface area. This geometric configuration results in rapid thinning of the fluid layer deposited on the top of the member. Once the fluid film thickness has reached the desired thickness, the fluid dispersal region ends.

The active region begins after the fluid dispersal region, though a transition or other region could be positioned between the fluid dispersal region and active region. Once in the active region, the fluid film thickness is controlled to achieve the desired result. In a seawater purification use, the fluid film would be maintained approximately constant. To achieve this result without altering the overall flow rate, the surface area of the active region may be decreased. That is, with some of the water evaporating off the surface in the active region, the film layer will get thinner unless the surface area is decreasing. By matching the rate of decrease in the surface area to the rate of evaporation, a generally constant fluid film thickness may be maintained. This allows for efficient heat transfer at optimum temperatures (e.g., about 140° F.). It prevents drying of the heat transfer surface, too.

If, on the other hand, it is desired to evaporate off certain components separately, then multiple dispersal and active regions could be used. Different heating levels also could be employed toward this end. The present invention provides sufficient flexibility to allow for these types of variations.

BRIEF DESCRIPTION OF THE DRAWINGS

FIG. 1 is a cross-sectional view of a preferred embodiment of the present invention.

FIG. 2 is a cross-sectional view of an alternative preferred embodiment of the present invention.

FIG. 3 is a cross-sectional view of an alternative preferred embodiment of the present invention.

FIG. 4 is a cross-sectional view of an alternative preferred embodiment of the present invention.

FIG. 5 is a perspective view of the embodiment of FIG. 4.

FIG. 6 is an illustration of the fluid film thickness profiles of various embodiments of the present invention.

FIG. 7 is a cross-sectional view of an embodiment of the invention used for growing algae.

FIG. 8 is a cross-sectional view of an embodiment of the invention used to collect hydrogen produced during the growth of algae.

FIG. 9 is a cross-sectional view of an embodiment of the invention used for solar distillation.

DETAILED DESCRIPTION

One expected use of the present invention is as a falling film evaporator. Such an evaporator is shown in cross-sectional view in FIG. 1. This embodiment of the invention may not be the most desired configuration for the purification of contaminated water, such as seawater. The embodiment shown in FIG. 1 is, however, an accurate representation of certain general characteristics of the present invention. FIG. 1, therefore, will be used to explain the basic structure and operation of the present invention.

A falling film evaporator 10 is shown in FIG. 1. Contaminated input liquid 12 is shown in an upper feed trough 14. A feed inlet 13 is shown, too, though the supply liquid can be provided in various ways. For example, rather than the dripping trough structure shown in FIG. 1, and inlet feed pipe or tube could be used, with its outlet positioned near the point where the liquid is shown dripping out of the trough 14. The structure and method used to supply the liquid to the apparatus is not central to the present invention.

A fluid flow member 16 is shown in the central area of FIG. 1. This member, and in particular, the variably curved surface of this member, represent key aspects of the invention. The fluid flow member 16 is separated into two important regions, a fluid dispersal region 18 and an active region 20. The liquid is quickly dispersed in the fluid dispersal region 18. That is, the fluid film thickness is quickly reduced in this region. The active region, on the other hand, is the region where maximum evaporation occurs, or where other activity occurs if the invention is not employed in an evaporator.

As the contaminated liquid 12 drips onto the upper area 21 of the fluid dispersal region 18, a relatively thick film layer is formed. The upper area 21 shown in FIG. 1 comes to a somewhat sharp point. In most actual embodiments of the present invention, it is expected that the upper area 21 would be less sharp or pointed than is shown in FIG. 1. Indeed, a relatively flat upper area 21 may be desirable in some applications. The slope of the curve of the outer member surface within the fluid dispersal region is dependent upon the nature of the fluid.

When water or other relatively thin liquids are used, a curvature such as that shown in FIG. 1 may be desirable. The desired outcome is a fluid film thickness that works best within the active region. With a water purification evaporator, for example, the fluid film with thin quickly. But if a thicker fluid is used, a much different curvature may be needed in the fluid dispersal region. An outer surface curve that is relatively flat at the top 21 will provide and highest rate of increase in surface area with decrease in elevation. In other words, a flatter upper area 21 will allow the fluid film to thin more with a given decrease in elevation. This may be needed for thicker fluids.

A parabolic curve is one preferred curvature for the outer surface of the fluid dispersal region 18. To generate the shape, a parabola is rotated around the vertical central axis 23. The central longitudinal axis 23 extends from the center of the upper end 21 to a point at the center of the generally cylindrical lower end 55. The shape of the fluid dispersal region 18 can be varied depending upon the specific parabola, or other type of curve, used. For thick fluids, a parabola with a flatter upper region would be desired, but for thinner fluids like water, a curve similar to that shown in FIG. 1 may be desirable. The present invention allows the designer to vary this aspect of the invention to best suit the particular needs of the application.

One possible application where a flatter upper end 21 may be desired would be the concentration of syrup, molasses, liquid malt extract, or other thick, sticky liquids. Such liquids flow slowly unless heated. By flowing such a liquid down the member 16 of the present invention, and allowing evaporation within the active region 20, the product may be substantially concentrated. This process may reduce the volume of weight of the material, thus allowing for easier storage or shipping. These applications of the invention are provided to show a specific situation in which a different curvature for the outer surface of the fluid dispersal region 18 might be desired.

A relatively thick layer of fluid 22 is shown near the upper end 21. As the fluid flows through the fluid dispersal region 18 it thins. A thinner film layer 24 is shown near the lower end of the fluid dispersal region 18. This is the film thickness as the fluid enters the active region 20. An active film thickness 26 is shown within the active region 20. In FIG. 1, this film thickness 26 is shown as approximately constant within the active region 20. That result is shown for illustration purposes only, because a different geometry is needed in the active region 20 to achieve that result in an evaporator. Fluid that did not evaporate 34, is collected at the lower end of the structure and exhausted from the apparatus by outlet 46.

Evaporated vapor 40 leaves the outer surface of the member 16, with most evaporation occurring within the active region 20. The vapor 40 rises and is removed from the apparatus through outlet 44. The outer housing 42 shown in FIG. 1 is illustrative only, as any suitable housing may be used. In fact, in a practical embodiment of the present invention, there may be multiple members 16 constructed as a group. In this variation, the contaminated or concentrated liquid outlet 46 and the water vapor outlet 44 may be common to multiple members 16.

Within the member 16, there may be heated fluid inlet tube 32 with an inlet 30 and an outlet 36. Steam 28 is shown flowing up the tube 32 and then down to the outlet 36. As the steam flows back down, it is exposed to the inner surface 50 of the member 16. The surface of the member 16 is heated in this manner, and may thus evaporate some of the fluid flowing down the surface.

The member 16 is closed at the top (i.e., the area in which the liquid is initially deposited), and the lower end 55 is shown open in FIG. 1. An open lower end 55 allows heat to be supplied to the member 16. The lower end 55, however, may be closed if there is not need for external heat. Whether the lower end 55 is open or closed, an inner chamber 25 is formed. The inner chamber 25, of course, is only accessible if the lower end 55 is open.

The active region 20 is generally cylindrical, and is shown in FIG. 1 with a generally constant radius. This geometry is represented by the same diameters A shown at the upper and lower ends of the active region 20 in FIG. 1. As will be explained below, the invention uses different geometries for the active region 20 to achieve different results for the fluid film.

The arrows used in FIGS. 1-4 show the flow paths of the different fluids. Using FIG. 1 for illustrative purposes, the single-line arrows represent liquids, while the double-line arrows represent gases. The liquid feed enters through inlet 13, as shown by the arrow. A similar, single-line arrow shows the flow of the liquid down the outside surface of member 16 and then out the outlet 46. Evaporation of some of the liquid produces water vapor 40, which rises and then exits the device through vapor outlet 44, as shown by the double-line arrows. Steam used to supply heat to the device is shown with double-line arrows within the inner chamber 25. Steam 28 is shown flowing up the tube 32 (by double-line arrows) and then down to the outlet 36 (again represented by the double-line arrows). The same arrow arrangement is used in other figures to represent the flow of fluids within the device.

Figure 2:
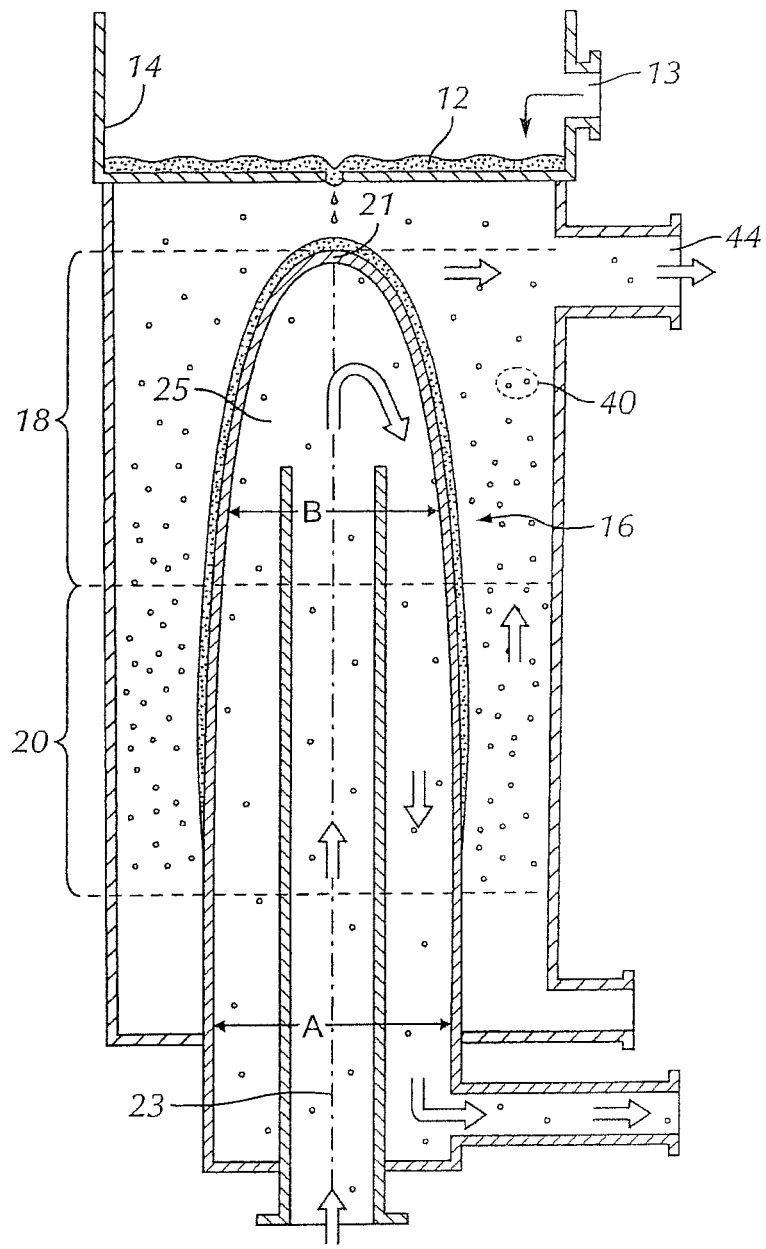
Figure 3:
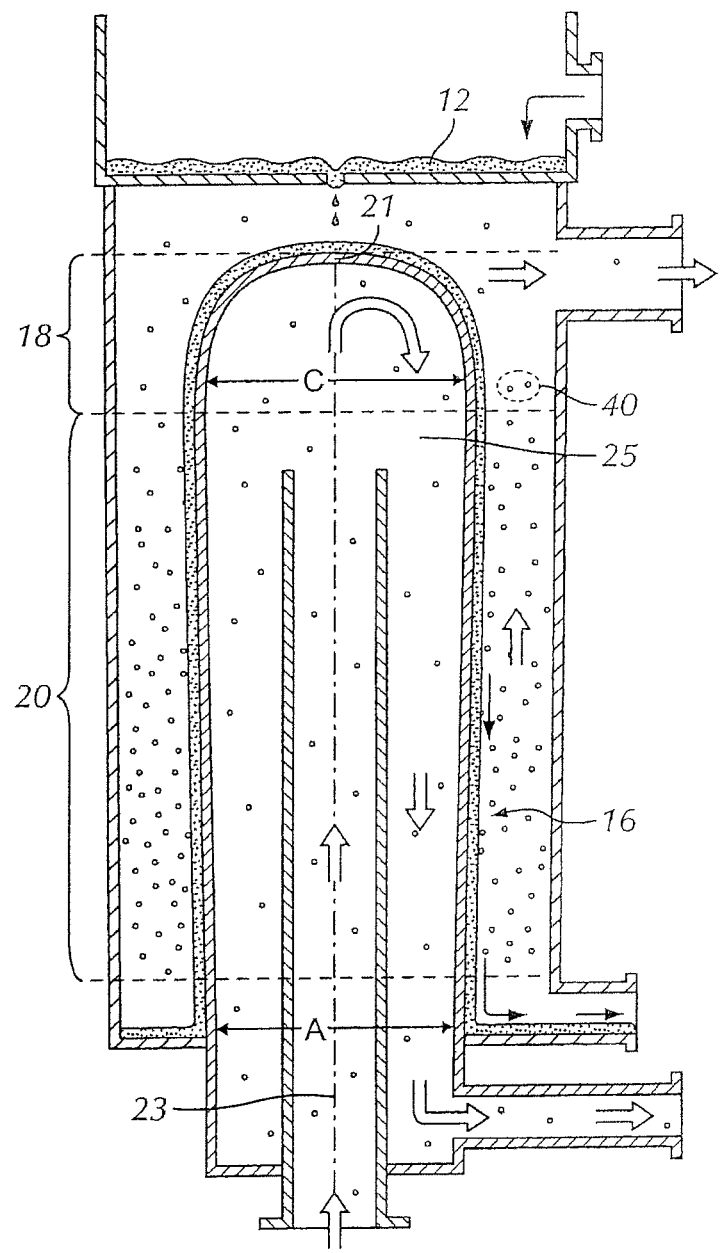

FIGS. 2 and 3 show important variations on the embodiment shown in FIG. 1. Each of these figures shows a different curvature in both the fluid dispersal region 18 and the active region 20. FIG. 2, for example, shows a flatter upper end 21 in the fluid dispersal region 18. This curvature will give fluids more time to thin as the fluids flow down the member 16.

The active region 20 in FIG. 2 is significantly different from the active region 20 of FIG. 1. In FIG. 1, the active region 20 has a relatively constant cross sectional area. That is, in FIG. 1, the active region 20 is generally cylindrical, with the diameters represented by A and B being approximately equal. Diameter A represents the diameter of the lower end of the active region 20. Diameter B, on the other hand, shows the diameter of the upper end of the active region 20, that is, of the point where the fluid dispersal region 18 ends and the active region 20 begins. In FIG. 1, diameters A and B are roughly equal, and the outer surface area within the active region 20 is not increasing or decreased as one moves along the longitudinal axis 23.

In FIG. 2, however, the active region 20 is quite different. Diameter A is now larger than diameter B. In other words, the upper part of the active region 20 in FIG. 2 has less surface area than the lower part. The surface area is increasing in the active region 20 in the direction of flow (i.e., downward). The rate of increase of the surface area within the active region 20, however, is less than the rate of increase in surface area within the fluid dispersal region 18.

This different configuration produces markedly different results. The same inner chamber 25 is shown in FIG. 2 and steam is supplied to that chamber 25 to heat the member 16, just as in FIG. 1. The heated surface results in evaporation, thus removing some of the liquid from the surface. Because the surface area is increasing and the amount of fluid remaining on the surface is decreasing, the fluid film thickness will continue to decrease in the active region 20 of FIG. 2. This result is illustrated by the vapor 40 ending some distance above the lower end of the member 16, and by the complete elimination of the film layer at a point above the lower end of the member 16.

The flow path arrows helps show this dynamic. Liquid is fed into the trough 14 through the inlet 13, as shown by the single-line arrow. Double-line arrows show the gaseous form of the material evaporating from the outer surface of the member 16. Note that no liquid lines are shown leaving the lower end of the device in FIG. 2, because all the liquid is evaporated in this embodiment.

The complete evaporation of the feed liquid may be undesirable in some applications, such as seawater purification systems. Nevertheless, it may be desirable in other contexts. If for example, it were desired to completely evaporate the entire liquid being supplied to the apparatus, using the configuration shown in FIG. 2 would greatly enhance the chances of achieving this outcome. FIG. 2 shows how the curvature of the surface of the active region 20 can be used to substantially vary the performance of the apparatus.

FIG. 3 shows another variation, and this one may be more suitable for a seawater purification system. In this embodiment, the upper end 21 of the fluid dispersal region 18 is relatively flat. This allows for rapid thinning of the fluid film thickness. It also allows for more of the length of the element 16 to be used for evaporation, which may be desirable.

The active region 20 shown in FIG. 3 has a decreasing surface area in the downward direction along the longitudinal axis 23. This can be seen by the difference in the diameters A and C. Diameter A is at the lower end of the active region 20, and it is shown to be approximately the same diameter as that shown in FIGS. 1 and 2. Diameter C, on the other hand, is at the upper end of the active region 20, near the point where the active region 20 meets the fluid dispersal region 18. Diameter C is larger than diameter A, meaning that the outer surface area of the active region 20 is decreasing as the fluid flows downward.

The embodiment shown in FIG. 3 may be suitable for a seawater purification system. By decreasing the surface area with decreasing elevation within the active region 20, an approximately constant fluid film thickness may be achieved. As in FIGS. 1 and 2, vapor 40 is shown evaporating from the fluid as is flows through the active region 20. If the surface area decreases at the same rate as fluid evaporates from the fluid film, a constant film thickness may be achieved. This is a highly desirable result because it prevents drying of the surface (i.e., and thus reduces scale build-up) and allows for maximum thermal efficiency.

Figure 4:
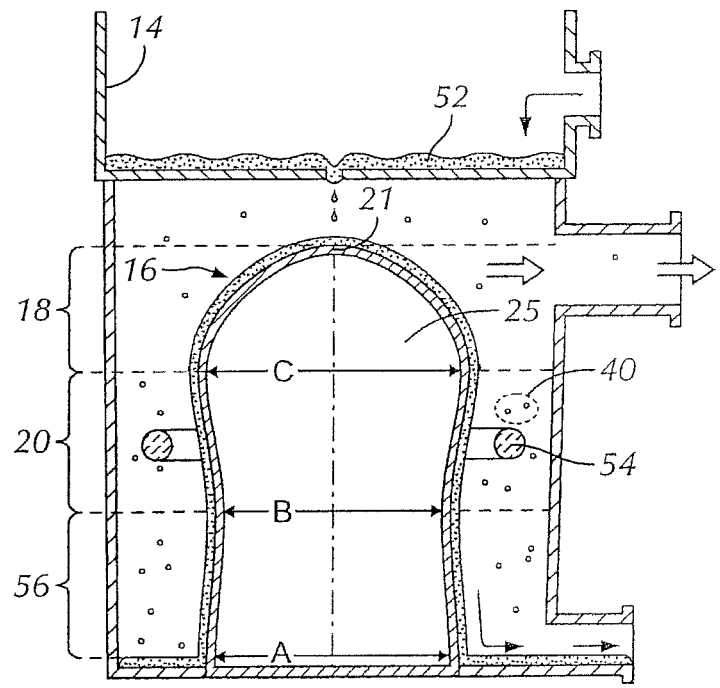
Figure 5:
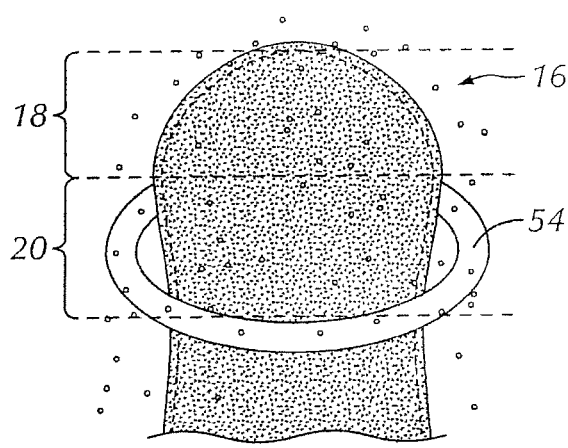

FIGS. 4 and 5 show the invention used in an algae-based carbon capture apparatus. The member 16 is shown with a closed upper and lower end. This may be desired in this embodiment for simplicity of design and because there may not be a need for a means of heating the inner chamber 25. Algae 52 are shown in the feed trough 14. The algae are deposited on the upper end 21 of the fluid dispersal region 18, where the algae 52 thin to a layer thickness appropriate for carbon capture.

The active region 20 in FIG. 4 is that area in proximity to the light source 54, shown as a light ring in cross section in FIG. 4. Some evaporation 40 may occur, but it may be desirable to minimize evaporation in this embodiment.

The member 16 shown in FIG. 4 has three distinct regions. The fluid dispersal region 18 and active region 20 are present, as in prior drawings. In FIG. 4, the active region is somewhat similar to that shown in FIG. 3. That is, the surface area decreases in the active area in the direction (i.e., downward) of the algae flow. This accounts for some evaporation, while keeping the algae film at a generally constant thickness. If no evaporation is expected, the active region 20 for this embodiment may be shaped like that shown in FIG. 1.

The third region in FIG. 4 is a recovery region 56. In this region, the algae cease functioning because they are too far from the light source. The algae flow though the recovery region 56 and are then collected for further use. A recovery region 56 as shown in FIG. 4 may be included in any embodiment of the invention, but may be less desirable is space is at a premium. For example, in a water purification system, it may be desirable to use as much of the member 16 as possible for heat transfer and evaporation, thus increasing the productivity of the apparatus.

FIG. 5 is a perspective view of the carbon capture apparatus of FIG. 4. The fluid dispersal region 18 and active region 20 are shown, with the light ring 54 surrounding the active region 20. The member 16 is shown in FIG. 5 without any housing or other structure. This illustration is provided to give a perspective image of the invention.

Figure 6:
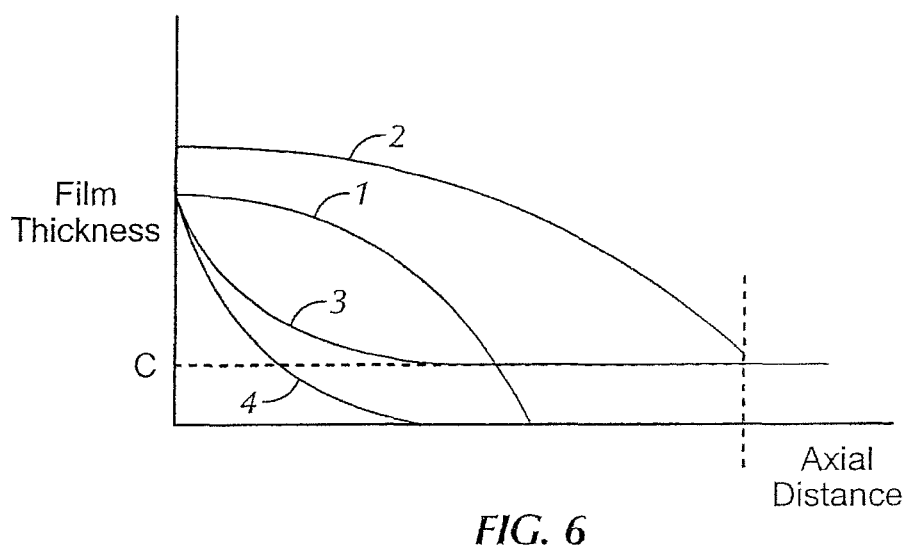

FIG. 6 is a series of curves that illustrate the performance of the invention with different geometries. Curve 1 shows possible performance of an embodiment like that shown in FIG. 1. The upper end 21 of the fluid dispersal region 18 of FIG. 1 has a relatively sharp point. This shape will allow the fluid to flow downward without a great deal of thinning. This result is illustrated in FIG. 6 by the relatively flat section at the start of Curve 1. In this part of Curve 1, the film thickness decreases rather slowly with axial distance (i.e., with decrease in elevation for a vertically oriented member 16). The film thickness begins to decrease more rapidly as the distance increases because of evaporation. If there is sufficient evaporation, or insufficient flow rate, the film thickness may decrease to zero, as shown for Curve 1.

There are ways to prevent the film thickness from decreasing to zero in the embodiment represented by Curve 1. Either the flow rate may be increased, the heat input may be decreased, or a combination of the two. If these changes are made, it is possible to maintain flow along the entire length of member 16, as is shown in Curve 2. This curve, however, represents suboptimal evaporation (i.e., because the fluid film is thicker) and, therefore, may not be a desirable result.

Curve 3 shows the result of the embodiment shown in FIG. 3. The flatter upper end 21 of the fluid dispersal region 18 results in a rapid thinning of the fluid layer thickness, as shown in Curve 3. The film thickness decreases until it reaches a constant level, denoted by the constant C. This film thickness is maintained by decreasing the surface area of the active region 20 in proportion to the evaporative losses, as explained above in connection with FIG. 3.

Curve 4 shows the result of using the embodiment of FIG. 2. A relatively flat upper end 21 is used, thus producing rapid reduction of the film thickness in the fluid dispersal region. But the film thickness continues to decrease in Curve 4 because the surface area continues to increase in the active region 20 of the embodiment shown in FIG. 2. This results in the film thickness being reduced to zero, quite possibly at a point relatively far up the length of the member 16. This result is illustrated by Curve 4 of FIG. 6.

Figure 7:
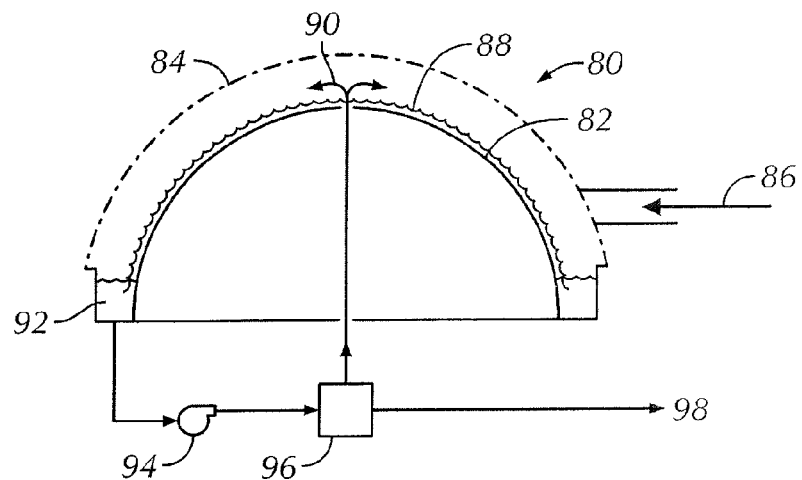

An embodiment of the invention for use as an algae growing device 80 is shown in FIG. 7. The apparatus 80 is designed for exposure to sunlight. It has an outer transmissive dome 84 over the upper fluid flow surface 82. The outer dome 84 in a preferred embodiment is transparent to sunlight and is made of a material that can retain its structural strength and transparency over long periods of exposure to UV light. It is further preferred that the device 80 be configured to allow for relatively easy replacement of the outer dome 84, so that the outer dome 84 may be replaced if it loses enough of its transparency to reduce the efficiency of the device 80.

Sunlight enters through the dome 84 and provides the energy for the algae growth process. Carbon dioxide is input to the device through a flow path 86 that may take the form of a pipe, hose, a series of hoses, or any other common means to inject the carbon dioxide into the area between the flow surface 82 and the outer, transparent dome 84.

The algae 90 is deposited at or near the top of the fluid flow surface 82, and gravity induces downward flow along the surface. This results in a thin layer of algae 88 of relatively constant thickness along the flow surface 82. The thickness of the layer can be varied by altering the rate at which the algae is deposited onto the surface. The curvature of the flow surface may be designed into distinct flow regions, as explained above in connection with a more general embodiment of the invention.

The algae reproduces through a photosynthetic reaction, consuming energy from sunlight and absorbing carbon dioxide. This process has been described in detail in numerous sources and is well known in the art. Through use of this process, carbon can be removed from the atmosphere, an application commonly called carbon capture. The embodiment of the present invention shown in FIG. 7 may be used for carbon capture purposes.

As the algae flows down the flow surface 82, it reaches a trough area 92. A pump 94 may be used to remove algae from the trough 92. A three-way valve 96 may be used to direct some algae flow back to the flow surface and excess algae 98 out of the system. The excess algae may be used for any other suitable purpose. This embodiment may be used to grow particular strains of algae for specific purposes, such as for food or animal feed. A combined algae production and carbon capture system is made possible with this embodiment of the invention.

The embodiment shown in FIG. 7 is a simple device that can be constructed at relatively low cost. It can be used near facilities that produce large amounts of carbon dioxide, such as many industrial facilities and fossil fuel power plants. The large, open domed region provides a large area for the algae to interact with sunlight and carbon dioxide. Maintaining a relatively constant algae film thickness enhances the efficiency of the process.

Figure 8:
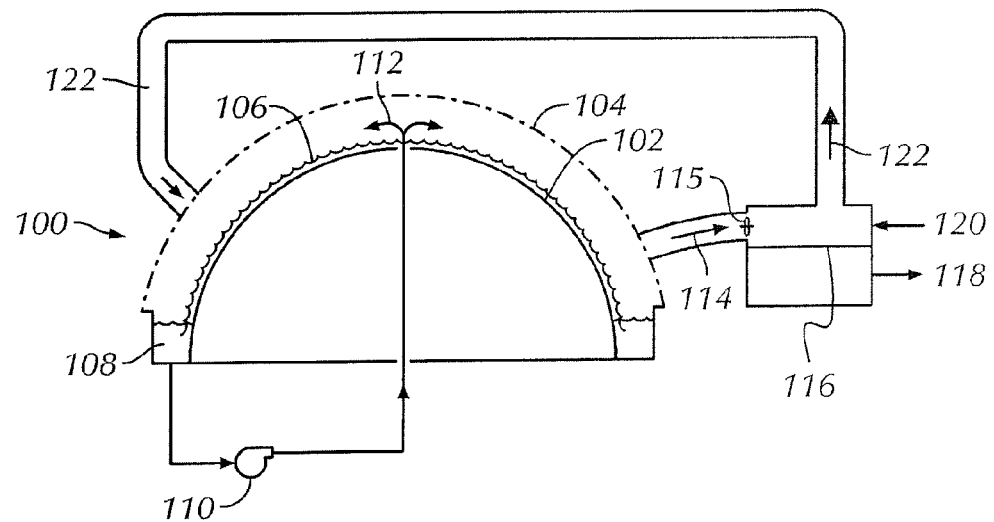

Another embodiment of the invention is shown in FIG. 8. This algae growth device 100 is similar to the one shown in FIG. 7, but this system is designed to also produce hydrogen. Hydrogen has potential to become an important fuel in the future, and the algae growth embodiments of the present invention provide a means for producing hydrogen gas for other uses. In the device 100, a transparent outer dome 104 is positioned outside an algae flow surface 102. Algae 112 is deposited onto the flow surface 102 at or near the top of the surface. Gravity-induced flow of the algae results in a thin algae film 106 along much of the flow surface 102. A trough 108 and pump 110 are shown and may be used for collecting and transporting the algae. Though not shown, some means for removing excess algae from the device may also be used. A three-way valve (as shown in FIG. 7) or a separate algae removal system (e.g., a separate line and pump or an overflow system) may be used for this purpose. These components of the device 100 are the same or very similar to the components described above in connection with FIG. 7.

The hydrogen production device 100 also has a carbon dioxide input 120 through a flow path 122. The carbon dioxide and sunlight interact with the flowing algae in the same way described above. This device 100, however, also has a water vapor extractor 114, which is shown as a vapor extraction line in FIG. 8. A fan 115 may be used to facilitate the flow of the water vapor. A hydrogen separation means 116 is then used to separate the hydrogen from the oxygen in the water vapor. A hydrogen permeable membrane is known in the art and will work for this purpose. An electrolysis process also could be used to separate the hydrogen gas. Any other means of separating the hydrogen from water vapor may be used for this purpose, as the invention is not limited in this regard.

Once separated from the water vapor, the hydrogen is removed through an extraction line 118. The oxygen and some of the unseparated water vapor may be combined with the incoming carbon dioxide flow path 122, as shown in FIG. 8. Alternatively, the water vapor extraction line could be entirely separate from the carbon dioxide input path 122. This arrangement is not shown, but could be used, for example, if the oxygen, water, and hydrogen were all to be recovered from the process.

The hydrogen produced by the invention can be either stored for later use or supplied directly to another apparatus as fuel. The storage option is expected to be more common, as the hydrogen may be stored onsite in appropriate containers for later use, or may be shipped by pipeline to another location for storage. But it is also possible to use the hydrogen produced by the invention directly as a fuel source. This may be useful in particular situations.

Though not shown in FIG. 7 or 8, it may also be desirable to maintain a particular temperature range within the device, or at least within the active carbon capture region of the device. Different strains of algae have distinct characteristics, including differing temperatures for optimal photosynthesis and growth. Some algae strains may be damaged for too high temperatures and others may require certain temperatures for photosynthesis to occur at a desire rate. To make the device operate at peak efficiency for a particular algae strain and particular conditions, it may be desirable to implement a temperature control means. If the algae growth and carbon capture processes are subject to only the normal daily cycle of sunlight exposure, the temperature within the device could vary a great deal. During the early part of the day, the temperature could be too low for optimal photosynthesis, but at mid-day and during the early afternoon period, the internal temperature could become too hot for optimal operation. The heating effect produced by the large, transmissive outer dome 84 may result in very high temperatures during the mid-day period.

A wide variety of means could be used to control the temperature within the device. Vent fans or other ventilation devices could be used to introduce or circulate cooler air into the space between the outer dome 84 and the flow surface 82. The carbon dioxide supply line could be cooled or heated, as needed to help control the internal device temperature. An external heating or cooling source could be used to cool the algae flow surface from the inside, as shown and explained above in connection with FIGS. 1-4. Coolers or heaters could be used to actively cool or heat the air within the space between the flow surface 82 and the outer dome 84. If the temperature tends to rise too much during the day, some type of external covering could be placed over part of the outer dome 84. The uppermost part of the outer dome 84, for example, is positioned over the algae dispersal region rather than the active carbon capture region. Covering this part of the outer dome 84 would have a relatively low impact on the carbon capture rate of the device, particularly if such covering is done only when the sunlight is at peak intensity. Any of these means could be used, alone or in combination with other means, to control the temperature within the device.

Figure 9:
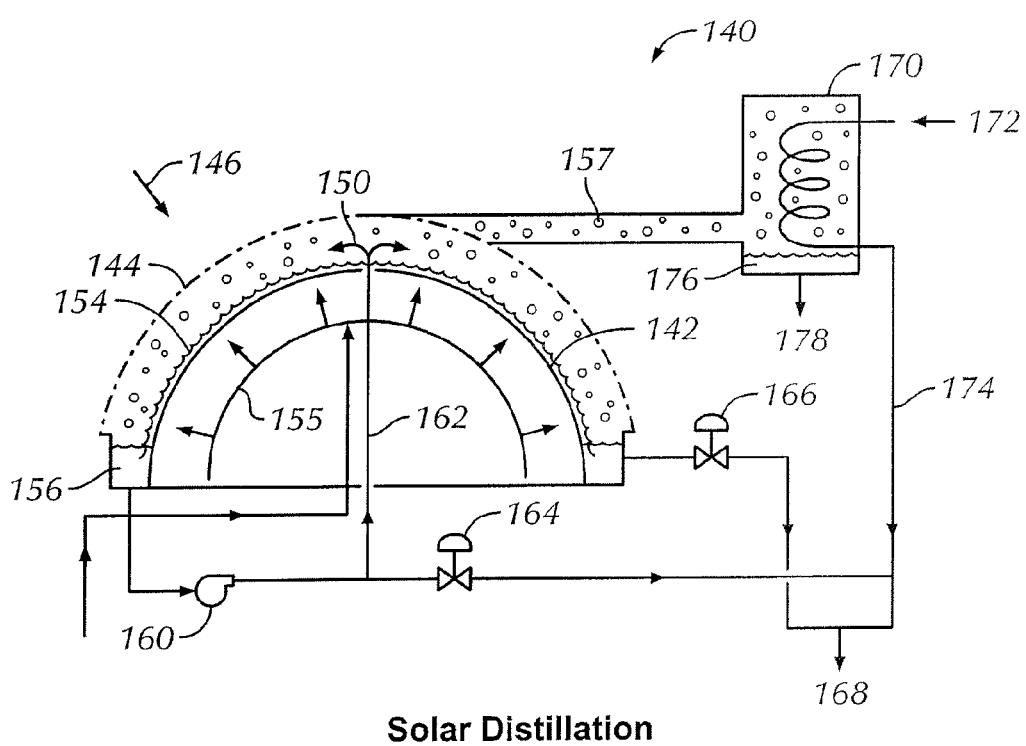

A solar distillation embodiment of the invention 140 is shown in FIG. 9. In this device, sunlight 146 is used as the evaporative energy source for the distillation process. This use of natural sunlight has certain advantages. First, many regions most in need of potable water receive a great deal of sunlight. Saudi Arabia, for example is both in need of more potable water and experiences a high number of clear, sunny days in a typical year. The natural concurrence of these two factors in many locations makes a sunlight-powered distillation device like the one shown in FIG. 9 a particularly important device.

Seawater 150 is shown entering the flow region in FIG. 9, where it is deposited on the fluid flow surface 142. A transmissive outer dome 144 (e.g., the dome may be transparent in a preferred embodiment) is positioned over the flow surface 142 in much the same manner as described in connection with FIGS. 7 and 8 above. In the solar distillation device 140, the transparent dome 144 may be constructed of glass or some other material that tends to enhance the heating from the sunlight.

The flow surface 142 is configured to produce a relatively constant thickness fluid layer 152 along much of the surface 142. This is done in the same manner described above. Maintaining a relatively thin film layer of constant thickness enhances the evaporative process, while also preventing the drying out of the flow surface. If the flow surface dries in areas, it will be more prone to scale formation, corrosion, or other problems. Keeping the entire flow surface 142 covered by a thin, flowing water film is an important advantage provided by the present invention.

The distillation device 140 shown in FIG. 9 is not intended to shown the actual geometrical configuration needed to obtain a constant film thickness. The specific geometry required will depend upon various factors, as explained above, and these factors may vary from one location and use to another. It is also important to note that the current invention allows for maintenance of a relatively constant film thickness, but it may not be necessary to maintain a high degree of constancy in all uses. For example, in the distillation context, it may be more important to keep the entire surface covered than to maintain a perfectly constant film thickness. Keeping a relatively thin film over a large part of the flow surface 142 provides the key advantages of the present invention.

An optional additional heat source may be used with the distillation device 140. The heat 155 could be applied to the inner side of the flow surface 142. Optimum temperature for seawater evaporative distillation is about 140 degrees Fahrenheit. At this temperature, enough water evaporates for the distillation process, while the temperature is low enough to reduce the amount of hard scale build up on the flow surface 142. This relationship was explained above, and is applicable to the solar distillation device 140, as well. When the outside temperature is low, the optional heat source could be used to maintain the flow surface 142 near a constant 140 degrees Fahrenheit. In many locations, however, the device 140 may work quite well without any external heat source.

It is quite possible that in some contexts the surface temperature of the flow surface 142 could exceed 140 degrees Fahrenheit merely from solar heating. In some regions, the sunlight is quite intense. With the heating effect of a transparent outer dome 144, the temperature within the evaporative region could easily become too high near mid-day in such regions. It may be necessary, therefore, to provide a cooling system to keep the temperature within a desired range. The cooling could take any of the forms mentioned above. In addition, increasing the flow rate of the seawater input could be used to control the temperature of the flow surface 142.

In some situations, it may be desired to heat the flow surface 142 early and late in the day for optimal evaporation, while it may also be desirable to cool the same surface 142 near mid-day due to excessive solar heating. This combined heating and cooling approach may be used to increase the efficiency and output of the distillation device throughout the day. All of these configurations and combinations are within the scope of the temperature control means, as that phrase is used herein.

The present invention, particularly in the embodiment shown in FIG. 9, offers the potential for a simple, efficient, and low-maintenance seawater distillation system. It is known in the art that evaporation of seawater (or other water with high levels of mineral salts) at temperatures above 140° F. leads to hard scale build-up on the evaporative surfaces. In typical seawater distillers, a heated fluid is circulated through a tube or sheet type heat exchanger. Heat is transferred to the seawater, some of which evaporates and is then condensed into potable water. This type of heated fluid distillation plant has been in used for many years. This prior art system works, but has several disadvantages. When the tube or sheet surface is heated to above 140° F., scale begins to build up on the heat transfer surfaces. This scale then reduces the efficiency of the heat transfer.

Removing scale from seawater distillers is a common practice, and one of the more common methods used for removing such scale is to introduce chemical cleaning agents into the system. These chemicals are often dangerous to plants and animals, and either cannot be discharged into the environment or must be greatly diluted before such discharge may be done. Storage of these chemicals poses additional costs and risks. If the tubes or sheets of the heat exchangers are pitted, these harsh chemicals may worsen such damage, leading to leaks. A leak in a tube or sheet can lead to an expensive repair or to isolation of the leaking section, which only serves to further reduce the efficiency of the distiller.

These problems can be avoided if the distillation process is conducted at or below 140° F. In typical prior art distillers, such a low operating temperature is not efficient. When the temperature of a bulk volume of water is at a certain point (e.g., 140° F.), that temperature reflects the mean kinetic energy of the many water molecules within the volume being measured. Some of those molecules are likely to have sufficient kinetic energy to evaporate. This localized evaporation, however, can occur only if a molecule with sufficient kinetic energy is also at or very near the surface of the liquid water. If the molecule is covered by too many lower energy water molecules, the high energy molecule may lose energy before it reaches the surface. When that happens, the molecule does not undergo evaporation.

The consequences of these facts are important for a seawater distiller. To avoid scale build up, it is desirable to operate at a relatively low temperature (i.e., at or below 140° F.). But at such temperatures, efficient evaporation is only possible if a thin film of liquid water is maintained on the evaporative surface. Maintaining a thin film over a large evaporative surface was not possible with prior art distillers, but is possible with the present invention. It is this capability of the present invention that allows the solar distillation system shown in FIG. 9 to operate efficiently at or below 140° F.

Operating efficiently within this temperature range provides important additional benefits. Because scaling is rarely a problem, there is less down-time for cleaning. And because scale cleaning is rarely required, the harsh and dangerous chemicals commonly used in prior art seawater distillers are not required by the present invention. This reduces the need for these chemicals, thus reducing costs and risks to the operator and the environment. Moreover, because the present invention operates well at lower temperatures, little, if any, external heat is needed, making the system simpler and less-expensive to construct and operate. All of these important advantages flow from the present invention's ability to maintain a relatively constant, thin, flowing, liquid film over a large evaporative surface. Making the system operate using the sun's energy as the primary, and possibly sole, energy input, produces a highly cost-effective solution to the potable water needs of many regions of the world. It should be noted that many of the regions facing the most intense potable water needs also experience a large number of clear sunny days at high temperatures. Such conditions are ideal for operation of the embodiment of the present invention shown in FIG. 9.

As the water film 154 flows over the surface 142, some of the water evaporates into water vapor 157. The water that does not evaporate collects in a trough area 156. This collected water will have a higher contaminant level than the incoming water to the system. In a seawater distillation unit, this means the collected water will have a higher salinity level. This water may be removed using a pump 160. Some of the pump's output could be combined with fresh input water (though not shown in FIG. 9) and redirected to the upper area of the flow surface through a feed line 162. Alternatively, the feed line 162 could be supplied directed with seawater along. This alternate construction is not shown in FIG. 9, but is easily understood. Which arrangement is used will depend upon local design choices.

The high salinity water from the pump 160 may flow through a control valve 164, which can be used to control the amount of flow out of the system and the amount of flow that is recirculated with incoming feed water. The excess high salinity water (or water with a higher level of other contaminants if seawater is not the feed water) exits the system through exhaust line 168. An outflow control valve 166 is also shown in FIG. 9 and can be used to direct flow directly from the trough area 156 to the exhaust line 168.

The water vapor is removed by a water vapor extractor 157, which directs the water vapor to a condenser 170. Seawater or other cooling fluid 172 flows through the condenser 170 to cool the water vapor 157 and produce pure liquid water. A pure water supply line 178 provides the distilled water from the unit. The water vapor extractor 157 may be a simple line positioned near an upper point of the outer dome 144, as the water vapor will tend to rise and drift out if the condensor is positioned at or above the point at which the vapor leaves the evaporative region. The cooling effect of the condensor creates a heat sink, while the evaporative surface is a heat source. By positioning the heat sink above the heat source, natural circulation of the water vapor will occur. This may be adequate in some circumstances, and allows for a simple design requiring little external power for operation.

It is expected, however, that the natural flow of the water vapor may be inadequate in some situations. If this occurs, the water vapor extractor may need to incorporate a fan, blower or some other means to inducing a more rapid flow of water vapor from the evaporative region to the condensor 170. Though such means are not shown in FIG. 9, use of fans or other means to create more flow are well-known in the art. An in-line fan is shown in the water vapor exhaust line in FIG. 8 (i.e., in connection with the hydrogen production embodiment of the invention).

The condenser cooling fluid 172 may exit through an return line 174. This return flow may then be mixed with the excess water in the exhaust line 168. A seawater distillation unit provides a good example of this operation. Seawater is both the supply water to the distillation plant and the cooling water from the condenser. The high salinity seawater that has not evaporated may have such a high salt content that it could have undesired environmental consequences if pumped directly into the environment in undiluted form. This problem can be eliminated by combining the high salinity seawater with the typical salinity seawater from the condenser. This combination dilutes the high salinity seawater enough to avoid any unwanted results. The combined exhaust seawater may then be returned directly to the sea through exhaust line 168.

While the preceding description is intended to provide an understanding of the present invention, it is to be understood that the present invention is not limited to the disclosed embodiments. To the contrary, the present invention is intended to cover modifications and variations on the structure and methods described above and all other equivalent arrangements that are within the scope and spirit of the following claims.

We claim:

1. A method of growing algae comprising:
   a. supplying algae to an algae flow surface configured to maintain a desired thickness of flowing algae within an active carbon capture region, wherein the algae flow surface is generally vertical and further comprises:
      i. an algae dispersal region extending radially outward and downward from an upper point of the flow surface, the algae dispersal region being defined by a surface curvature that produces an increasing surface area configured to reduce the thickness of a flowing algae film; and,
      ii. the active carbon capture region extending from a point below the algae dispersal region, the active carbon capture region being defined by a surface curvature selected to maintain a desired algae film thickness within the active carbon capture region;
   b. exposing the flowing algae to sunlight;
   c. supplying carbon dioxide to the flowing algae while the flowing algae is exposed to the sunlight.

2. The method of claim 1, further comprising:
   a. removing water vapor from the flowing algae; and,
   b. separating hydrogen from the removed water vapor.

3. The method of claim 1, further comprising:
   a. collecting algae after it has flowed over the algae flow surface;
   b. reintroducing some of the collected algae to the algae flow surface; and,
   c. harvesting some of the collected algae.

4. The method of claim 1, wherein the flowing algae is exposed to sunlight that is transmitted through an exterior dome positioned radially outward from the algae flow surface.

5. The method of claim 3, further comprising processing some of the harvested algae for use in biofuel.

6. The method of claim 3, further comprising harvesting some of the harvested algae for use as animal food.

7. The method of claim 2, wherein the step of separating hydrogen from the removed water vapor is performed by exposing the water vapor to a hydrogen permeable membrane.

8. A method of growing algae comprising:
   a. supplying algae to generally vertical algae flow surface configured to maintain a desired thickness of flowing algae;
   b. exposing the flowing algae to sunlight that, is transmitted through an exterior dome positioned radially outward from the algae flow surface; and,
   c. supplying carbon dioxide to the flowing algae while the flowing algae is exposed to the sunlight.

9. The method of claim 8, further comprising:
   a. removing water vapor from the flowing algae; and,
   b. separating hydrogen from the removed water vapor.

10. The method of claim 8, further comprising:
    a. collecting algae after it has flowed over the algae flow surface;
    b. reintroducing some of the collected algae to the algae flow surface; and,
    c. harvesting some of the collected algae.

11. The method of claim 8, further comprising extracting oils from the harvested algae.

12. The method of claim 8, further comprising processing some of the harvested algae for use in animal food.

13. A method of growing algae comprising:
    a. supplying algae to generally vertical algae flow surface configured to maintain a desired thickness of flowing algae;
    b. exposing the flowing algae to sunlight;
    c. supplying carbon dioxide to the flowing algae while the flowing algae is exposed to the sunlight;
    d. removing water vapor from the flowing algae; and,
    e. separating hydrogen from the removed water vapor by exposing the water vapor to a hydrogen permeable membrane.

14. The method of claim 13, further comprising:
    a. collecting algae after it has flowed over the algae flow surface;
    b. reintroducing some of the collected algae to the algae flow surface; and,
    c. harvesting some of the collected algae.

15. The method of claim 13, wherein the flowing algae is exposed to sunlight that is transmitted through an exterior dome positioned radially outward from the algae flow surface.

16. The method of claim 14, further comprising extracting oils from the harvested algae.

17. The method of claim 14, further comprising processing some of the harvested algae for use in animal food.

* * * * *